(12) United States Patent
Islam (10) Patent No.: US 12,235,218 B2
(45) Date of Patent: Feb. 25, 2025

(54) COMPOSITIONS AND METHODS FOR THE ASSESSMENT OF SOIL QUALITY

(71) Applicant: Ohio State Innovation Foundation, Columbus, OH (US)

(72) Inventor: Khandakar Islam, Upper Arlington, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 804 days.

(21) Appl. No.: 17/271,768

(22) PCT Filed: Sep. 3, 2019

(86) PCT No.: PCT/US2019/049312
§ 371 (c)(1),
(2) Date: Feb. 26, 2021

(87) PCT Pub. No.: WO2020/047538
PCT Pub. Date: Mar. 5, 2020

(65) Prior Publication Data
US 2022/0128481 A1    Apr. 28, 2022

Related U.S. Application Data

(60) Provisional application No. 62/726,171, filed on Aug. 31, 2018.

(51) Int. Cl.
| | | |
|---|---|---|
| *A01C 21/00* | (2006.01) | |
| *G01N 1/38* | (2006.01) | |
| *G01N 21/80* | (2006.01) | |
| *G01N 33/24* | (2006.01) | |

(52) U.S. Cl.
CPC ........... *G01N 21/80* (2013.01); *A01C 21/007* (2013.01); *G01N 1/38* (2013.01); *G01N 33/24* (2013.01); *G01N 33/245* (2024.05)

(58) Field of Classification Search
CPC .......... G01N 21/80; G01N 1/38; G01N 33/24; G01N 2033/245; A02C 21/007
See application file for complete search history.

(56) References Cited

U.S. PATENT DOCUMENTS

| | | | |
|---|---|---|---|
| 5,028,543 A | 7/1991 | Finch et al. | |
| 8,091,275 B2 * | 1/2012 | Bissonnette | C05G 5/23 71/34 |
| 2006/0088939 A1 | 4/2006 | Rajendram | |
| 2008/0273925 A1 | 11/2008 | Borden et al. | |

(Continued)

FOREIGN PATENT DOCUMENTS

CN    1559994 A    1/2005

OTHER PUBLICATIONS

International Search Report and Written Opinion issued by the International Searching Authority (ISA/US) in PCT Application No. PCT/US2019/049312 on Nov. 20, 2019. 8 pages.

(Continued)

*Primary Examiner* — Jill A Warden
*Assistant Examiner* — Michael Stanley Gzybowski
(74) *Attorney, Agent, or Firm* — Meunier Carlin & Curfman LLC (57) ABSTRACT

Disclosed are methods of measuring the quantity of active organic matter in a soil sample, as well as kits for performing such measurements.

19 Claims, 8 Drawing Sheets

| Soil quality | Poor Soil | Fair Soil | Good Soil | Excellent Soil |
|---|---|---|---|---|
| Soil organic matter [%] | > 0 - 1 | > 1 - 2.5 | > 2.5 - 4.5 | > 4.5 |
| Active organic matter [kg/ha] | > 0 - 400 | > 400 - 800 | > 800 - 1600 | > 1600 |
| Available nitrogen [kg/ha] | > 0 - 12 | > 12 - 26 | > 26 - 40 | > 40 |
| Microbial biomass [kg/ha] | > 0 - 300 | > 300 - 630 | > 630 - 1280 | > 1280 |
| Aggregate stability [%] | > 0 - 25 | > 25 - 40 | > 40 - 70 | > 70 |

(56) References Cited

U.S. PATENT DOCUMENTS

2016/0223502 A1    8/2016    Kirkpatrick

OTHER PUBLICATIONS

Weil, Ray R., et al. "Estimating active carbon for soil quality assessment: A simplified method for laboratory and field use." American Journal of Alternative Agriculture (2003): 3-17.
Schindelbeck, Robert R., et al. "Comprehensive assessment of soil quality for landscape and urban management." Landscape and Urban Planning 88.2-4 (2008): 73-80.
Culman, S., et al., "Procedure for the Determination of Permanganate Oxidizable Carbon," 2017, 5 pages.
Stiles, C. A., et al. "Validation Testing of a Portable Kit for Measuring an Active Soil Carbon Fraction," Soil Science Society of America Journal, vol. 75, No. 6, 2011, pp. 2330-2340.
Extended European Search Report, dated Jun. 1, 2022, received in connection with corresponding EP Patent Application No. 19853979.3.
Australian Intellectual Property Office. Examination Report. Issued in AU Application No. 2019333326 on Jun. 26, 2024. 4 pages.
Indian Patent Office. Examination Report issued in Indian Application No. 202117014188 on Mar. 6, 2023. 5 pages.
Canadian Intellectual Property Office. Office Action issued in Canadian Application No. 3111201 on Mar. 1, 2024. 6 pages.

\* cited by examiner

| Soil quality | Poor Soil | Fair Soil | Good Soil | Excellent Soil |
|---|---|---|---|---|
| Soil organic matter [%] | > 0 - 1 | > 1 - 2.5 | > 2.5 - 4.5 | > 4.5 |
| Active organic matter [kg/ha] | > 0 - 400 | > 400 - 800 | > 800 - 1600 | > 1600 |
| Available nitrogen [kg/ha] | > 0 - 12 | > 12 - 26 | > 26 - 40 | > 40 |
| Microbial biomass [kg/ha] | > 0 - 300 | > 300 - 630 | > 630 - 1280 | > 1280 |
| Aggregate stability [%] | > 0 - 25 | > 25 - 40 | > 40 - 70 | > 70 |

FIGURE 1

| HANNA Checker® Reading | Active C (lbs./A) | Active OM (kg/ha) | HANNA Checker® Reading | Active C (lbs./A) | Active OM (kg/ha) |
|---|---|---|---|---|---|
| 0 | >1900 | >2125 | 3.1 | 1009 | 1130 |
| 0.1 | 1891 | 2117 | 3.2 | 980 | 1098 |
| 0.2 | 1861 | 2085 | 3.3 | 951 | 1065 |
| 0.3 | 1832 | 2052 | 3.4 | 921 | 1032 |
| 0.4 | 1802 | 2019 | 3.5 | 892 | 999 |
| 0.5 | 1773 | 1986 | 3.6 | 862 | 966 |
| 0.6 | 1744 | 1953 | 3.7 | 833 | 933 |
| 0.7 | 1714 | 1920 | 3.8 | 804 | 900 |
| 0.8 | 1685 | 1887 | 3.9 | 774 | 867 |
| 0.9 | 1656 | 1854 | 4 | 745 | 834 |
| 1 | 1626 | 1821 | 4.1 | 716 | 801 |
| 1.1 | 1597 | 1788 | 4.2 | 686 | 768 |
| 1.2 | 1567 | 1756 | 4.3 | 657 | 736 |
| 1.3 | 1538 | 1723 | 4.4 | 627 | 703 |
| 1.4 | 1509 | 1690 | 4.5 | 598 | 670 |
| 1.5 | 1479 | 1657 | 4.6 | 569 | 637 |
| 1.6 | 1450 | 1624 | 4.7 | 539 | 604 |
| 1.7 | 1421 | 1591 | 4.8 | 510 | 571 |
| 1.8 | 1391 | 1558 | 4.9 | 481 | 538 |
| 1.9 | 1362 | 1525 | 5 | 451 | 505 |
| 2 | 1333 | 1492 | 5.1 | 422 | 472 |
| 2.1 | 1303 | 1459 | 5.2 | 392 | 440 |
| 2.2 | 1274 | 1427 | 5.3 | 363 | 407 |
| 2.3 | 1244 | 1394 | 5.4 | 334 | 374 |
| 2.4 | 1215 | 1361 | 5.5 | 304 | 341 |
| 2.5 | 1186 | 1328 | 5.6 | 275 | 308 |
| 2.6 | 1156 | 1295 | 5.7 | 246 | 275 |
| 2.7 | 1127 | 1262 | 5.8 | 216 | 242 |
| 2.8 | 1097 | 1230 | 5.9 | 187 | 209 |
| 2.9 | 1068 | 1196 | 6 | 157 | 176 |
| 3 | 1039 | 1163 |  |  |  |

FIGURE 2A

| HANNA Checker® Reading | Active C (lbs./A) | Active OM (kg/ha) | HANNA Checker® Reading | Active C (lbs./A) | Active OM (kg/ha) |
|---|---|---|---|---|---|
| 0 | >2850 | >3200 | 3.1 | 1514 | 1696 |
| 0.1 | 2836 | 3176 | 3.2 | 1470 | 1646 |
| 0.2 | 2792 | 3127 | 3.3 | 1426 | 1597 |
| 0.3 | 2748 | 3078 | 3.4 | 1382 | 1548 |
| 0.4 | 2704 | 3028 | 3.5 | 1338 | 1498 |
| 0.5 | 2660 | 2979 | 3.6 | 1294 | 1449 |
| 0.6 | 2616 | 2929 | 3.7 | 1250 | 1400 |
| 0.7 | 2572 | 2880 | 3.8 | 1206 | 1350 |
| 0.8 | 2527 | 2831 | 3.9 | 1162 | 1301 |
| 0.9 | 2483 | 2781 | 4 | 1117 | 1252 |
| 1 | 2439 | 2732 | 4.1 | 1073 | 1202 |
| 1.1 | 2395 | 2683 | 4.2 | 1029 | 1153 |
| 1.2 | 2351 | 2633 | 4.3 | 985 | 1103 |
| 1.3 | 2307 | 2584 | 4.4 | 941 | 1054 |
| 1.4 | 2263 | 2535 | 4.5 | 897 | 1005 |
| 1.5 | 2219 | 2485 | 4.6 | 853 | 955 |
| 1.6 | 2175 | 2436 | 4.7 | 809 | 906 |
| 1.7 | 2131 | 2387 | 4.8 | 765 | 857 |
| 1.8 | 2087 | 2337 | 4.9 | 721 | 807 |
| 1.9 | 2043 | 2288 | 5 | 677 | 758 |
| 2 | 1999 | 2239 | 5.1 | 633 | 709 |
| 2.1 | 1955 | 2189 | 5.2 | 588 | 659 |
| 2.2 | 1911 | 2140 | 5.3 | 544 | 610 |
| 2.3 | 1867 | 2091 | 5.4 | 500 | 561 |
| 2.4 | 1823 | 2041 | 5.5 | 456 | 511 |
| 2.5 | 1778 | 1992 | 5.6 | 412 | 462 |
| 2.6 | 1734 | 1943 | 5.7 | 368 | 413 |
| 2.7 | 1690 | 1893 | 5.8 | 324 | 363 |
| 2.8 | 1646 | 1844 | 5.9 | 280 | 314 |
| 2.9 | 1602 | 1795 | 6 | 236 | 265 |
| 3 | 1558 | 1745 | | | |

COMPOSITIONS AND METHODS FOR THE ASSESSMENT OF SOIL QUALITY

CROSS-REFERENCE TO RELATED APPLICATIONS

This application is a national stage application filed under 35 U.S.C. § 371 of PCT/US2019/049312 filed Sep. 3, 2019, which claims benefit of U.S. Provisional Application No. 62/726,171, filed Aug. 31, 2018, which is hereby incorporated herein by reference in its entirety.

BACKGROUND

Global food security and agricultural management practices are changing in dynamic and remarkable ways under global climate change scenarios. While conventional apiculture produces greater amounts of food, feed, and fiber, the high-input current practices have affected soil quality/health with reduced agroecosystem services. By 2050, Earth's population is projected to increase 34 percent to reach 9.2 billion people. Global food production must increase by 70 percent to compensate for this population growth, requiring farmers and growers to be increasingly efficient, informed and sustainable. The challenges and opportunities that are emerging with the advent of expanding evidence-based knowledge, technology and information systems forcing us to envision climate-smart agricultural renaissance in the $21^{st}$ century to improve soil health for sustaining hungry world. Precision agriculture, as an important component of the sustainable management practices, is the use of real-time data on weather, disease and weed pressures, air and water quality, soil quality/health, and crop maturity to perform predictive and valid analytics to make instant, smarter, reliable, and more efficient decisions.

Soil health, like human health, is a complex, integrated, and holistic concept. The NRCS defines soil health as the continued capacity of soil to function as a vital living ecosystem that sustains plants, animals, and humans and maintains environmental quality with an ecological harmony. Thus, soil health not only relates to the soil biological, chemical and physical properties, but also to its functionality and productivity. Improved soil health enhances the resilience of croplands to extreme weather events, and directly impacts local business, jobs and the economic stability of rural communities. Farmers, educators, consultants, master gardeners, state and federal personnel, and other professionals are increasingly interested in making simple, rapid, precise, reliable and economic assessments of field soil quality to help guide soil-crop-water management decisions. However, such a simple, consistent and rapid field test for routine evaluation of agricultural soil quality/health is not yet commercially available in the market.

Historically, soil organic matter (SOM) is considered as an integral component of soil that influences many critical functions, properties and/or processes, including biological diversity, efficiency and energy-flow; chemical reactions and buffering [oxidation-reduction, ion-exchange capacity, and nutrient cycling]; and physical flow and stability [water infiltration, compaction, and aggregate stability]. As such, the SOM is considered as the most widely acknowledged core composite indicator of soil quality (health). However, the amount and quality of SOM depend on functional distribution of various organic carbon pools in the terrestrial ecosystems as represented by:

$$SOM = f(G+R+D+L+V+T_m+B_m+A_m)$$

where G is the green biomass, R is the below-ground biomass, D is the debris, L is the liter, V is the below-ground dead mass, $T_m$ is the translocated phytomass, $B_m$ is the microbial biomass, and $A_m$ is the animal mass.

As SOM is thermodynamically unstable, the balance between two basic processes of primary production and microbial decomposition and transformation largely determines the carbon (~58%) accumulation and quality (lability) of SOM. Of particular importance is the biochemically labile organic carbon pool, which appears to be more dynamic to agricultural management practices than the bulk total carbon in SOM. Based on relative bio-availability, carbon in SOM can be broadly divided into two major pools: (i) a readily metabolizable or available (ACME) carbon pool (referred to as active carbon or active organic matter) that microbes utilize quickly and consistently as a food and energy source. This active carbon pool is composed of simple carbohydrates, amino acids and sugars, root exudates, partially decomposed plant and animal residues, microbial biomass and their metabolites that are not intricately bound to the mineral constituents, all of which are susceptible to further decomposition with a half-life in days to a few years; and (ii) a passive carbon pool (i.e., the passive organic matter) that varies from very slowly decomposable to resistant (humic materials) in nature due to structural complexity and physico-chemical protection by clays and minerals (such as Calcium) which lead to stability in soil with a half-life of in decades to millennia. About 5 to 25% of SOM is in active pool.

Although both active organic matter and passive organic matter pools of SOM contribute to soil ecosystem function and stability, the active carbon pool has by far the greater influence on most effects of SOM considered beneficial to soil quality and agroecosystem services. The active carbon pool circulates and recycles through biological, chemical and physical pools to maintain a delicate balance on soil functions and processes and processes. Therefore, achieving a particular total SOM level is far less important than maintaining a constant metabolism and turnover of active carbon with respect to soil quality. So, the values of total organic carbon or SOM normally reported in commercial soil analysis lab reports are of very little use in assessment of soil quality, as compared with the active carbon content in the soil. Accordingly, simple, reliable, rapid and globally accessible field methods for evaluating the levels of active carbon (and by extension the quality of soil) are needed urgently for sustainable agricultural management practices and food security in response to climate effects.

SUMMARY

Disclosed herein method for assessing a quantity of active organic matter. The methods can comprise (a) contacting the soil sample with an aqueous solution comprising a permanganate salt, an inorganic flocculant, and a pH buffering agent; and (b) evaluating the aqueous solution to assess the quantity of active organic matter in the soil sample.

The permanganate salt acts as an oxidant and colorimetric indicator which preferentially oxidizes that labile (active) fraction of SOM. This oxidation-reduction reaction (redox) simulates natural enzymatic ability to distinguish active organic matter from passive organic matter. The oxidation of SOM is accompanied by a vibrant color change, providing a readily visible colorimetric response which can be associated with the quantity of active organic matter in the soil sample. The permanganate salt can be present in the aqueous solution at a concentration of from 0.01 M to 0.05 M (e.g., a concentration of from 0.01 M to 0.03 M, such as about 0.02M). In certain embodiments, the permanganate salt can comprise potassium permanganate.

The pH buffering agent can be present in an amount effective to buffer the aqueous solution at a suitable pH for performing a reproducible assay that can consistently and accurately account for variations in active carbon content among soils under diverse management practices. The pH buffering agent can buffer the aqueous solution at a mildly acidic pH (a pH of less than 7). In some embodiments, the aqueous solution can be buffered at a pH of from 5 to less than 7 (e.g., a pH of from 5.5 to 6.5, such as a pH of about 6). In some embodiments, the pH buffering agent can be present in the aqueous solution at a concentration of from 0.0005 M to 0.01 M (e.g., a concentration of from 0.0005 M to 0.005 M, such as about 0.001 M).

In some embodiments, the pH buffering agent can act as both a buffering agent and an inorganic complexing agent. In these embodiments, the pH buffering agent can also complex with colored ions present in the soil sample which may interfere with the colorimetric assay, such as iron, manganese, or a combination thereof. In certain embodiments, the pH buffering agent can comprise a phosphate salt, such as dipotassium phosphate.

The inorganic flocculant serves to help rapidly settle (precipitate) dispersed soil particles (clays and fine silt) during the assay. The inorganic flocculant can be present in the aqueous solution at a concentration of from 0.01 M to 0.2 M (e.g., about 1 M). In sonic embodiments, the inorganic flocculant can comprise a chloride salt. In certain embodiments, the inorganic flocculant can comprise a chloride salt consisting of calcium chloride, aluminum chloride, and combinations thereof. In certain cases, the inorganic flocculant can exhibit a positive enthalpy of solvation in water. In these embodiments, dissolution of the inorganic flocculent can produce exothermic heat (heat of solution), facilitating the complete dissolution of components [especially the permanganate salt] present in solution with the inorganic flocculant.

Step (a) can comprise, for example, combining the soil sample and the aqueous solution in a vessel; agitating the soil sample and the aqueous solution; and incubating the soil sample and the aqueous solution.

The soil sample and the aqueous solution can be incubated for a period sufficient to allow the dispersed soil particles to settle out of the aqueous solution, a period of time sufficient to allow a color of the aqueous solution to equilibrate, or a combination thereof. In some embodiments, the soil sample and the aqueous solution can be incubated for a period of from 30 seconds to 15 minutes.

In some embodiments, combining the soil sample and the aqueous solution in a vessel can comprise combining the soil sample, a reagent composition, and an aqueous fluid in the vessel, wherein the reagent composition comprises the permanganate salt, the inorganic flocculant, and the pH buffering agent. In some cases, the reagent composition can comprise a reagent stock solution (e.g., an aqueous solution comprising the permanganate salt, the inorganic flocculant, and the pH buffering agent). In other cases, the reagent composition can comprise a solid (e.g., a tablet or powder comprising the permanganate salt, the inorganic flocculant, and the pH buffering agent). In these embodiments, combining the soil sample and the aqueous solution in a vessel can comprise dissolving the solid reagent composition (e.g., the tablet or powder) in an aqueous fluid to form the aqueous solution.

In some embodiments, the method can further comprise harvesting one or more soil samples from an agricultural field. In some cases, the method comprises harvesting a plurality of soil samples from different locations within the agricultural field to obtain an overall picture of the quantity of active organic matter across the agricultural field. The soil sample(s) can be dried (e.g., allowed to sit in direct sunlight for a period) prior to contacting step (a).

The colorimetric response observed upon contacting the soil sample with an aqueous solution can be assessed by a variety of suitable methods to determine the concentration of active organic matter in the soil sample. If desired, one or more additional soil quality parameters (e.g., microbial biomass, basal respiration, total nitrogen content, active nitrogen content, particulate organic carbon, aggregate stability, soil quality, or any combination thereof) can be derived/predicted from the quantity of active organic matter in the soil sample. If desired, a projected crop yield and/or projected relative crop yield can also be determined from the quantity of active organic matter in the soil sample.

Also provided are kits for assessing the quantity of active organic matter in a soil sample. The kits can be used in conjunction with the methods described herein. The kits can comprise a testing vessel (e.g., a graduated glass bottle); a reagent composition comprising a permanganate salt, an inorganic flocculant, and a pH modifying agent; and instructions for using the kit to assess the quantity of active organic matter in the soil sample as a measure of soil quality and associated properties. In some cases, the kit can further comprise a digital colorimeter or spectrophotometer. In some embodiments, the kit can further comprise a color chart comprising a plurality of colors and a concentration of active organic matter corresponding to each of the plurality of colors. In some embodiments, the kit can further comprise a lookup table that lists concentrations of active organic matter in soil samples for a plurality of absorbance values. In some embodiments, the kit can include a code (e.g., a digital code, such as a QR code) for downloading software such as an app which can assist in interpreting the results of the colorimetric assay. For example, the software can prompt the user to capture a digital image of the reacted solution in the testing vessel, and provides the used with the corresponding concentration of active organic matter in the soil sample (e.g., based on an analysis of the RGB values as described above). If desired, the software can also provide the used with one or more additional soil quality parameters (e.g., microbial biomass, basal respiration, total nitrogen content, active nitrogen content, particulate organic carbon, aggregate stability, soil quality, or any combination thereof) derived from the quantity of active organic matter in the soil sample. if desired, a projected crop yield and/or projected relative crop yield can also be provided.

In some cases, the reagent composition comprises a reagent stock solution. For example, the reagent stock solution comprises an aqueous solution comprising from 0.05 M to 0.5 M (e.g., from 0.1 M to 0.3 M) potassium permanganate; from 0.1 M to 1.5 M (e.g., from 0.75 M to 1.25 M) calcium chloride; from 0.01 M to 0.5 M (e.g., from 0.075 M to 0.125 M) aluminum chloride; and from 0.005 M to 0.1 M (e.g., from 0.0075 M to 0.0125 M) dipotassium phosphate. In one embodiment, the reagent stock solution can comprise an aqueous solution comprising about 0.2 M potassium permanganate; about 1 M calcium chloride; about 0.1 M aluminum chloride; and about 0.01 M dipotassium phosphate. In other embodiments, the reagent composition can comprise a solid, such as a tablet or powder.

Also described herein are agricultural methods that employ the test kits and test methods described herein. The methods can comprise, for example, methods for top-dressing or side-dressing a crop with a fertilizer. For example, provided herein are methods for cultivating a crop in an agricultural field that comprise planting the crop in the agricultural field; allowing the crop to reach at least a seedling stage; collecting a soil sample from the agricultural field; determining a quantity of active organic matter in the soil sample using the methods described herein; deriving a quantity of active nitrogen in the soil sample from the quantity of active organic matter measured in the soil sample; and applying a supplemental amount of nitrogen fertilizer to the agricultural field if desirable for the crop being cultivated. In some embodiments, the method can comprise applying a nitrogen fertilizer to the agricultural field when the quantity of active nitrogen in the field is less than 40 kg/ha. In some embodiments, the method can comprise applying an effective amount of a nitrogen fertilizer to the agricultural field to increase the quantity of active nitrogen in soil to at least 40 kg/ha. In certain embodiments, the crop can comprise corn, and allowing the crop to reach at least a seedling stage can comprise allowing the corn to grow to the V6 stage. Based on the active organic matter and active nitrogen tests at V6 stage, a right amount of supplemental fertilization (side dressing at 100 to 150 kg N/ha) can be applied for optimum crop growth. Similarly, nitrogen fertilization can be used for sorghum and millet. For wheat, spelt, triticale, and barley, early spring application of nitrogen fertilization can be done, based on active organic matter and active nitrogen contents. For sunflower, fertilization rates can be determined based on active organic matter and active nitrogen tests performed before planting or side dressing can be used at V6 to V8 stages. For high-value vegetable crops, nitrogen fertilization rates can be determined based on active organic matter and active nitrogen tests performed before planting or during early growth by broadcasting or thru drip-irrigation. Similarly, for high-value fruit crops (such as strawberries), nitrogen fertilization rates can be determined based on active organic matter and active nitrogen tests performed annually at early spring or during growth by broadcasting or thru drip-irrigation.

DETAILED DESCRIPTION

Disclosed herein are methods for assessing a quantity of active organic matter in a soil sample. Active organic matter (also referred to as active carbon) refers to the labile pool of carbon that microbes utilize quickly and consistently as a food and energy source. The active carbon pool of SOM readily participates in biochemical reactions, redox cycles, and physical processes. This active carbon pool is composed of simple carbohydrates, amino acids and sugars, partially decomposed plant and animal residues, root exudates, microbial biomass and their metabolites that are not intricately bound to the mineral constituents, all of which are susceptible to further decomposition with a half-life in days to a few years. The methods can comprise (a) contacting the soil sample with an aqueous solution comprising a permanganate salt, an inorganic flocculant, and a pH buffering agent; and (b) evaluating the aqueous solution to assess the quantity of active organic matter in the soil sample.

Step (a) can comprise, for example, combining the soil sample and the aqueous solution in a vessel; agitating the soil sample and the aqueous solution; and incubating the soil sample and the aqueous solution.

The soil sample and the aqueous solution can be incubated for a period of time sufficient to allow the dispersed soil particles to settle out of the aqueous solution, a period of time sufficient to allow a color of the aqueous solution to equilibrate (e.g., to exhibit less than a 5% change in absorbance at the $\lambda_{max}$ absorption of the aqueous solution, as measured via a spectrophotometer), or a combination thereof.

In some embodiments, the soil sample and the aqueous solution can be incubated for a period of from at least 30 seconds (e.g., at least 1 minute, at least 5 minutes, or at least 10 minutes). In some embodiments, the soil sample and the aqueous solution can be incubated for a period of 30 minutes or less (e.g., 25 minutes or less, 20 minutes or less, 15 minutes or less, 10 minutes or less, or 5 minutes or less).

The soil sample and the aqueous solution can be incubated for a period ranging from any of the minimum values described above to any of the maximum values described above. For example, in some embodiments, the soil sample and the aqueous solution can be incubated for a period of from 30 seconds to 30 minutes (e.g., from 30 seconds to 15 minutes)

In some embodiments, combining the soil sample and the aqueous solution in a vessel can comprise combining the soil sample, a reagent composition, and an aqueous fluid in the vessel, wherein the reagent composition comprises the permanganate salt, the inorganic flocculant, and the pH buffering agent. In some cases, the reagent composition can comprise a reagent stock solution (e.g., an aqueous solution comprising the permanganate salt, the inorganic flocculant, and the pH buffering agent). In other cases, the reagent composition can comprise a solid (e.g., a tablet or powder comprising the permanganate salt, the inorganic flocculant, and the buffering agent). In these embodiments, combining the soil sample and the aqueous solution in a vessel can comprise dissolving the solid reagent composition (e.g., the tablet or powder) in an aqueous fluid to form the aqueous solution.

In some embodiments, the method can further comprise harvesting one or more soil samples from an agricultural field. In some cases, the method comprises harvesting a plurality of soil samples from different locations within the agricultural field to obtain an overall picture of the quantity of active organic matter across the agricultural field. The soil sample(s) can be dried (e.g., allowed to sit in direct sunlight for a period) prior to contacting step (a).

The methods described herein can be used to quantify active organic matter in any soil type, including red soils (e.g., iron rich soils), organic soils, rice soils, and other marginal or low fertility soils. Soils can be classified using the United States Department of Agriculture's soil taxonomy.

In some embodiments, the soil can comprise an alfisol. Alfisols are characterized by an argillic, natric, or kandic horizon. They exhibit high-to-medium base saturation and are moderately weathered. Alfisols are commonly formed under boreal or broadleaf forests. They are rich in iron and aluminum. Alfisols are relatively common in humid areas, semi-tropics, and Mediterranean climates, accounting for 9.6% of global and 14.5% of U.S. ice-free land.

In some embodiments, the soil can comprise an andisol. Andisols form from volcanic ejecta and are dominated by allophane or Al-humic complexes. Andisols are characterized by andic soil properties: high in poorly crystalline Fe and Al minerals, high in phosphorus, low bulk density, and high proportions of glass and amorphous colloidal materials, such as allophane, imogolite and ferrihydrite. Andisols generally exhibit a high organic matter content, and sometimes include melanic epipedon. Andisols account for 0.7% of global and 1.7% of U.S. ice-free land.

In some embodiments, the soil can comprise an aridisol. Aridisols are dry soils (i.e., they have iridic moisture regime). They often exhibit an ochric epipedon, and sometimes an argillic or natric horizon. In any case, aridisols must have some diagnostic subsurface horizon. Aridisols are commonly found in deserts, and accounting for 12.7% of global and 8.8% of U.S. ice-free land.

In some embodiments, the soil can comprise an entisol. Entisols exhibit the least soil profile development. An ochric epipedon is common, and no B horizons are present. Entisols are the most common order by surface area, accounting for 16.3% of global and 12.2% of U.S. ice-free land.

In some embodiments, the soil can comprise a gelisol. Gelisols are soils with permafrost within 100 cm or cryoturbation (frost churning) within 100 cm plus permafrost within 200 cm. Gelisols are common at high latitudes and elevations, accounting for 8.6% of global and 7.5% of U.S, ice-free land.

In some embodiments, the soil can comprise a histosol (organic-type soil). Histosols exhibit a histic epipedon, and usually possess an aquic soil moisture regime. Histosols do not exhibit diagnostic subsurface horizons. Histosols generally exhibit rapid decomposition when aerated. Histosols include peat or bog, with greater than 20% organic matter. Histosols are generally characterized by organic soil materials extending down to an impermeable layer or by an organic layer that is more than 40 cm thick and without andic properties. Histosols are commonly found in wetlands (swamps, marshes, etc.), accounting for 1.2% of global and 1.3% of U.S. ice-free land.

In some embodiments, the soil can comprise an inceptisol. Inceptisols are like entisols, but the beginning of a B horizon is evident. Inceptisols exhibit no diagnostic subsurface horizons. They are generally found in landscapes that are continuously eroded or include young deposits. Inceptisols can include an arabic, sulfuric, calcic, gypsic, petrocalcic, or petrogypsic horizon, or a mollic, cambric, or histic epipedon, or exhibit an exchangeable sodium percentage of greater than 15% or fragipan. Inceptisols account for 9.9% of global and 9.1% of U.S. ice-free land.

In some embodiments, the soil can comprise a mollisol. Mollisols exhibit a mollic epipedon and a high base saturation of at least 50%. Mollisols are dark soils, some of which exhibit argillic or natric horizons. Mollisols are common in grasslands, accounting for 6.9% of global and 22.4% of U.S. ice-free land.

In some embodiments, the soil can comprise an oxisol. Oxisols show the most soil profile development and are characterized by an oxic horizon within 150 cm of soil surface. They generally have low nutrient availability, no argillic horizon, and are highly weathered. Oxisols are dominated by end-member clays, Al, Mn and Fe oxides. Oxisols are commonly found in old landscapes in tropics, accounting for 7.6% of global and less than 0.01% of U.S. ice-free land.

In some embodiments, the soil can comprise a spodosol. Spodosols are characterized by a spodic horizon (ash color bleached) within 2 meters of soil surface without andic properties. Spodosols usually have an albic horizon. They are generally high in Fe, Mn, Al oxides and humus accumulation, and are acidic soils. Spodosols are common in coniferous or boreal forests, accounting for 2.6% of global and 3.3% of U.S. ice-free land.

In some embodiments, the soil can comprise an ultisol. Ultisols exhibit an argillic or kandic horizon, and low base saturation of less than 35% at 2 meters depth or 75 cm below a fragipan. Ultisols are common in subtropical regions and are often known as red clay soils. Ultisols account for 8.5% of global and 9.6% of U.S. ice-free land.

In some embodiments, the soil can comprise a vertisol. Vertisols typically exhibit a mollic epipedon. Vertisols are high in shrinking and swelling clays, including greater than 30% clay to a depth of 50 cm. Deep cracks (called gilgai) form when soil dries. Vertisols generally form from parent materials high in clay (e.g., shales, basins, exposed Bt horizons of old soils), and account for 2.4% of global and 1.7% of U.S. ice-free land.

In certain embodiments, the soil sample comprises an oxisol, a mollisol, an alfisol, an ultisol, an inceptisol, or any combination thereof.

The colorimetric response observed upon contacting the soil sample with an aqueous solution can be assessed by a variety of methods suitable to determine the concentration of active organic matter in the soil sample. In some embodiments, step (b) can comprise visually comparing a color of the aqueous solution with a color chart to determine the concentration of active organic matter in the soil sample, wherein the color chart comprising a plurality of colors and a concentration of active organic matter corresponding to each of the plurality of colors. In some embodiments, step (b) can comprise measuring an absorbance value of the aqueous solution using a spectrophotometer, and determining the concentration of active organic matter in the soil sample from the absorbance value using a standard curve that correlates absorbance values at a wavelength with concentrations of active organic matter in soil samples. In some embodiments, step (b) can comprise measuring an absorbance value of the aqueous solution using a colorimeter, and determining the concentration of active organic matter in the soil sample from the absorbance value using a lookup table that lists concentrations of active organic matter in soil samples for a plurality of absorbance values. In some embodiments, step (b) can comprise imaging the aqueous solution (e.g., using a digital camera), obtaining one or more RGB values from an image of the aqueous solution, and determining the concentration of active organic matter in the soil sample from the one or more RGB values using a lookup table that lists concentrations of active organic matter in soil samples for a plurality of RUB values. In certain embodiments, this can be performed using an application on a smartphone. In some embodiments, step (b) can comprise imaging the aqueous solution (e.g., using a digital camera), obtaining one or more RGB values from an image of the aqueous solution, and determining the concentration of active organic matter in the soil sample from the absorbance value using a standard curve that correlates one or more RGB values with concentrations of active organic matter in soil samples. In certain embodiments, this can be performed using an application on a smartphone.

If desired, one or more additional soil quality parameters (e.g., microbial biomass, basal respiration, total nitrogen content, active nitrogen content, particulate organic carbon, soil aggregate stability, soil quality, or any combination thereof) can be derived from the quantity of active organic matter in the soil sample. If desired, a projected crop yield and/or projected relative crop yield can also be determined from the quantity of active organic matter in the soil sample.

Permanganate Salts

The permanganate salt acts as an oxidant and color indicator which preferentially oxidizes that labile (active) fraction of SOM. This oxidation-reduction (redox) reaction simulates natural enzymatic ability to distinguish active organic matter from passive organic matter. The oxidation of organic matter is also accompanied by a vibrant color change, providing a readily visible colorimetric response which can be associated with the quantity of active organic matter in the soil sample.

The permanganate salt can comprise a permanganate salt or a combination of permanganate salts. The permanganate salt can include any alkali metal (i.e., Group IA or Group 1) cation, alkali earth metal (i.e., Group IIA or Group 2) cation, or an ammonium cation in addition to the manganate anion. For example, in some embodiments, the alkali or alkali earth metal cation may comprise Li, Na, K, Rh, Cs, Fr, Be, Mg, Ca, Sr, Ba and/or Ra. In some embodiments, the alkali metal or alkali earth metal cation comprises Li, Na, K, Rb, Cs, Be, Mg, Ca, Sr and/or Ba. For example, in some embodiments, the rare earth element comprises Na, K, Mg and/or Ca. Some nonlimiting examples of suitable permanganate salts include potassium permanganate, sodium permanganate, calcium permanganate, and ammonium permanganate. In certain embodiments, the permanganate salt can comprise potassium permanganate.

In some embodiments, the permanganate salt can be present in the aqueous solution at a concentration of at least 0.01 M (e.g., at least 0.02 M, at least 0.03 M, or at least 0.04 M). In some embodiments, the permanganate salt can be present in the aqueous solution at a concentration of 0.05 M or less (e.g., 0.04 M or less, 0.03 M or less, or 0.02 M or less)

The permanganate salt can be present in the aqueous solution at a concentration ranging from any of the minimum values described above to any of the maximum values described above. For example, the permanganate salt can be present in the aqueous solution at a concentration of from 0.01 M to 0.05 M (e.g., a concentration of from 0.01 M to 0.03 M, such as about 0.02 M).

pH Buffering Agents

The pH buffering agent can be present in an amount effective to buffer the aqueous solution at a suitable pH for performing a reproducible assay that can consistently and accurately account for variations in active carbon content among soil types. In some embodiments, the pH buffering agent can act as both a buffering agent and an inorganic complexing agent. In these embodiments, the pH buffering agent can also complex with colored ions present in the soil sample which may interfere with the colorimetric assay, such as iron, manganese, or a combination thereof. In certain embodiments, the pH buffering agent can comprise a phosphate salt, such as dipotassium phosphate.

The pH buffering agent can buffer the aqueous solution at a mildly acidic pH (a pH of less than 7). In some embodiments, the aqueous solution can be buffered at a pH of less than 7 (e.g., less than 6.75, less than 6.5, less than 6.25, less than 6.0, less than 5.75, less than 5.5, or less than 5.25). In some embodiments, the aqueous solution can be buffered at a pH of at least 5.0 (e.g., at least 5.25, at least 5.5, at least 5.75, at least 6.0, at least 6.25, at least 6.5, or at least 6.75).

The aqueous solution can be buffered at a pH ranging from any of the minimum values described above to any of the maximum values described above. For example, in some embodiments, the aqueous solution can be buffered at a pH of from 5 to less than 7 (e.g., a pH of from 5.5 to 6.5, such as a pH of about 6).

In some embodiments, the pH buffering agent can be present in the aqueous solution at a concentration of at least 0.0005 M (e.g., at least 0.001 M or at least 0.005 M). In some embodiments, the pH buffering agent can be present in the aqueous solution at a concentration of 0.01 M or less (e.g., 0.005 M or less or 0.001 M or less).

The pH buffering agent can be present in the aqueous solution at a concentration ranging from any of the minimum values described above to any of the maximum values described above. For example, in some embodiments, the pH buffering agent can be present in the aqueous solution at a concentration of from 0.0005 M to 0.01 M a concentration of from 0.0005 M to 0.005 M, such as about 0.001 M).

Inorganic Flocculants

The inorganic flocculant serves to help rapidly settle (precipitate) dispersed soil particles during the assay. The inorganic flocculant can be present in the aqueous solution at a concentration of from 0.01 M to 0.2 M (e.g., about 1 M).

Illustrative inorganic flocculants include, but are not limited to, salts comprising multivalent metal ions, such as but not limited to, aluminum, calcium or magnesium ions. In some embodiments, the inorganic flocculant can comprise a chloride salt. In certain embodiments, the inorganic flocculant can comprise a chloride salt selected from the group consisting of calcium chloride, aluminum chloride, and combinations thereof.

In certain cases, the inorganic flocculant can exhibit a positive enthalpy of solvation in water. In these embodiments, dissolution of the inorganic flocculent gives exothermic heat (heat of solution), facilitating the complete dissolution of components present in solution with the inorganic flocculant.

Agricultural Methods

Also described herein are agricultural methods that employ the test kits and test methods described herein. The agricultural methods can comprise determining the quantity of active organic matter in an agricultural field using a method described above, and selecting an appropriate management for the agricultural field in view of the quantity of active organic matter measured in the soil By way of example, in some embodiments the quantity of active organic matter in the soil can be at least 1600 kg/ha. In these embodiments, the soil can be excellent soil, which is biologically diverse and efficient, chemically buffered, physically stable, balanced, and productive. Accordingly, methods can include maintaining current management practices or reducing fertilization rates for an agricultural field from which the soil sample was collected. In some cases, methods can include applying a low amount (or zero) fertilizer and/or organic amendments to the agricultural field. In some embodiments, an appropriate crop can be selected based on the quantity of active organic matter measured and soil quality determined in the soil. For example, in some embodiments, methods can further comprise planting a row crop selected from the group consisting of common large grain crops [corn, soybeans, sunflower], small grain crops [millet, canola, wheat, spelt, triticale, barley, oats, sorghum] or a combination thereof in an agricultural field from which the soil sample was collected. In other embodiments, methods can further comprise engaging in horticulture or floriculture in an agricultural field from which the soil sample was collected.

In other embodiments, the quantity of active organic matter in the soil sample can be from 800 kg/ha to 1600 kg/ha. In these embodiments, the soil can be good soil which is biologically diverse, chemically buffered, physically stable, partially balanced, and to some extent productive. Accordingly, methods can further comprise changing or modifying current management practices using continuous no-till, cropping diversity, cover crops, soil and plant amendments for the agricultural field from which the soil sample was collected to improve soil quality. For example, in some examples, methods can comprise practicing crop rotation in the agricultural field from which the soil sample was collected. In some examples, methods can comprise planting a cover crop (e.g., legumes, grasses, rye, turnips, radish, or a combination thereof) in the agricultural field from which the soil sample was collected. In certain examples, methods can comprise planting a blend of cover crops in the agricultural field from which the soil sample was collected. In some example, methods can comprise adding an organic amendment, fertilizer, or a combination thereof to an agricultural field from which the soil sample was collected.

In other embodiments, the quantity of active organic matter in the soil sample can be from 400 kg/ha to 800 kg/ha. In these embodiments, the soil can be fair soil, which exhibits low biodiversity, is chemically unbuffered and inefficient, physically unstable, unbalanced, and exhibits low-medium productivity. Accordingly, methods can further comprise changing current management practices for the agricultural field from which the soil sample was collected to improve soil quality for economic crop production using continuous no-till, cropping diversity, cover crops, and soil and plant amendments. For example, in some examples, methods can comprise practicing crop rotation in the agricultural field from which the soil sample was collected. In some examples, methods can comprise planting a cover crop (e.g., legumes, grasses, rye, turnips, radish, or a combination thereof) in the agricultural field from which the soil sample was collected. In certain examples, methods can comprise planting a blend of cover crops in the agricultural field from which the soil sample was collected. In some example, methods can comprise adding an organic amendment, fertilizer, soil amendments like gypsum and zeolite, or a combination thereof to an agricultural field from which the soil sample was collected. In some example, methods can comprise engaging in no-till/low-till cultivation practices in the agricultural field from which the soil sample was collected.

In other embodiments, the quantity of active organic matter in the soil sample can be less than 400 kg/ha (i.e., from greater than 0 kg/ha to less than 400 kg/ha. In these embodiments, the soil can be poor soil that exhibits poor biodiversity and inefficiency, is chemically unbuffered, physically unstable, unbalanced, and exhibits low productivity. Accordingly, methods can further comprise mandatory changing of current management practices for the agricultural field from which the soil sample was collected to improve soil quality for economic crop production using continuous no-till, cropping diversity, cover crops, and soil and plant amendments. For example, in some examples, methods can comprise practicing crop rotation in the agricultural field from which the soil sample was collected. In some examples, methods can comprise planting a cover crop (e.g., legumes, grasses, rye, turnips, radish, or a combination thereof) in the agricultural field from which the soil sample was collected. In certain examples, methods can comprise planting a blend of cover crops in the agricultural field from which the soil sample was collected. In some example, methods can comprise adding an organic amendment, fertilizer, or a combination thereof to an agricultural field from which the soil sample was collected. In some example, methods can comprise adding an inorganic amendment (e.g., zeolite, lime, gypsum, or any combinations thereof) to the agricultural field from which the soil sample was collected. In some example, methods can comprise engaging in no-till/low-till cultivation practices in the agricultural field from which the soil sample was collected.

Also provided are methods for cultivating crops in conjunction with the methods for quantifying active carbon mater described herein. The methods can comprise, for example, methods for top-dressing or side-dressing a crop with a fertilizer. The amount of fertilizer added during the top-dressing or side-dressing can be determined from first assessing the quantity of active organic matter in the soil of an agricultural field using the methods described herein, then deriving the concentration of active nitrogen in the soil of the agricultural field from the quantity of active nitrogen, and then applying an appropriate amount of fertilizer to provide the final desired quantity of active nitrogen after top-dressing or side-dressing.

For example, provided herein are methods for cultivating a crop in an agricultural field that comprise planting the crop in the agricultural field; allowing the crop to reach at least a seedling stage; collecting a soil sample from the agricultural field; determining a quantity of active organic matter in the soil sample using the methods described herein; deriving a quantity of active nitrogen in the soil sample from the quantity of active organic matter measured in the soil sample; and applying a fertilizer to the agricultural field when the quantity of active nitrogen in the soil sample is less than 40 kg/ha. In some embodiments, applying a fertilizer to the agricultural field can comprise applying an effective or supplementary amount fertilizer to the agricultural field (e.g., an effective amount to increase the quantity of active nitrogen in the soil to at least 40 kg/ha). In certain embodiments, the crop can comprise corn, and allowing the crop to reach at least a seedling stage can comprise allowing the corn to grow to the V6 stage. Based on the active organic matter and active nitrogen tests at V6 stage, a right amount of supplemental fertilization (side dressing at 100 to 150 kg N/ha) can be applied for optimum crop growth. Similarly, nitrogen fertilization can be used for sorghum and millet. For wheat, spelt, triticale, and barley, early spring application of nitrogen fertilization can be done, based on active organic matter and active nitrogen contents. For sunflower, fertilization rates can be determined based on active organic matter and active nitrogen tests performed before planting or side dressing can be used at V6 to V8 stages. For high-value vegetable crops, nitrogen fertilization rates can be determined based on active organic matter and active nitrogen tests performed before planting or during early growth by broadcasting or thru drip-irrigation. Similarly, for high-value fruit crops (such as strawberries), nitrogen fertilization rates can be determined based on active organic matter and active nitrogen tests performed annually at early spring or during growth by broadcasting or thru drip-irrigation.

Kits

Also provided are kits for assessing the quantity of active organic matter in a soil sample. The kits can be used in conjunction with the methods described herein. The kits can comprise a testing vessel (e.g., a graduated glass bottle); a reagent composition comprising a permanganate salt, an inorganic flocculant, and a pH modifying agent; and instructions for using the kit to assess the quantity of active organic matter in the soil sample. In some cases, the kit can further comprise a colorimeter or spectrophotometer. In some embodiments, the kit can further comprise a color chart comprising a plurality of colors and a concentration of active organic matter corresponding to each of the plurality of colors. In some embodiments, the kit can further comprise a lookup table that lists concentrations of active organic matter in soil samples for a plurality of absorbance values.

In some cases, the reagent composition comprises a reagent stock solution. For example, the reagent stock solution comprises an aqueous solution comprising from 0.05 M to 0.5 M (e.g., from 0.1 M to 0.3 M) potassium permanganate; from 0.1 M to 1.5 M (e.g., from 0.75 M to 1.25 M) calcium chloride; from 0.01 M to 0.5 M (e.g., from 0.075 M to 0.125 M) aluminum chloride; and from 0.005 M to 0.1 M (e.g., from 0.0075 M to 0.0125 M) dipotassium phosphate. In one embodiment, the reagent stock solution can comprise an aqueous solution comprising about 0.2 M potassium permanganate; about 1 M calcium chloride; about 0.1 M aluminum chloride; and about 0.01 M dipotassium phosphate. In other embodiments, the reagent composition can comprise a solid, such as a tablet or powder.

By way of non-limiting illustration, examples of certain embodiments of the present disclosure are given below.

EXAMPLES

Example 1

Field Tests for Detecting and Quantifying Active Organic Matter

Farmers, educators, consultants, master gardeners, scientists, and state and federal personnel are increasingly interested in making simple, rapid, economic and reliable assessments of soil quality in response to management practices and expected climate change scenarios. Currently available university and private commercial soil testing labs are not providing comprehensive or simple soil health measurements, interpretation and management recommendations, based on soil biological, chemical and physical core indicator properties. The commercial soil testing costs range from $30 to $95 per sample or more. However, soil tests based on different approaches, indicators, tools, and scales offered by several university and private commercial labs often provide conflicting, variable, and confusing results without any realistic interpretations and management recommendations. Most private commercial soil labs do not even attempt to distinguish between active and passive organic matter pools in their routine analysis. Thus, farmers and growers are left to their own intuition for interpretation and adoption of soil health management practices.

Described herein is a stand-alone simple colorimetric assay for the rapid and most reliable quantification of active organic matter in a soil sample. The test can provide farmers with nearly instant information regarding soil health and provide management recommendations based on the quantification of active organic matter in the sample. The tests employ a pH-buffered dilute mild acidic potassium permanganate ($KMnO_4$) solution. The dilute $KMnO_4$ solution was used to perform short-term mild chemical oxidation of SOM simulating microbial decomposition of SOM, which is largely associated with biochemical oxidation-reduction (enzymatic) processes. However, several problems are associated with using $KMnO_4$ oxidation method to measure active organic matter, including (1) stability of solution pH and SOM oxidation, (2) complete color bleaching by higher SOM contents, (3) masking of pink color in red or colored soils, (4) stability of solution color, (5) problem with waterlogged or rice soils, and (6) reaction with biochar, charcoal, $CaCO_3$, etc.

Based on a series of tests conducted on different soils (~1,500 samples) collected worldwide, it was discovered that mild acidic 0.02 M $KMnO_4$ solution (buffered at pH 6) is a suitable reagent to determine active organic matter because (1) it quickly oxidizes the labile (C and N) pool of SOM, (2) dilute neutral solutions are more reactive and sensitive, (3) it serves as both reactant and indicator (visual bleaching effect), (4) it correlates with both deductive and inductive soil quality indicators, and (5) it is relatively safe to handle (0.006-0.3M solutions). Several salt and chemicals [$CaCl_2$, $Al(Cl)_3$, and $K_2HPO_4$] were added to maintain solution pH-stability, induce the rapid flocculation and settling of soil particles, remove colored ions in the sample that may mask the result of the colorimetric assay, and stability of color.

When mixed with completely to partially air-dried soil (2-minutes shaking), the pH-buffered mild acidic $KMnO_4$ solution reacts with most of the active carbon pool of SOM, causing a sharp color change from deep purple to a light pink or colorless. The lighter the pink color of the $KMnO_4$ solution after reacting with the soil, the greater the amount of active organic matter content, which indicates a higher-quality soil. Shades of dark purple or pink indicate poor, fair, and good soil quality; a very light pink or colorless mixture indicates excellent soil quality. The active organic matter test can be used to predict total SOM content, available (active) nitrogen, microbial biomass, particulate organic matter, and soil aggregate stability (e.g., using a color chart or a colorimeter (a Hanna®). These tests were calibrated and validated for global use with different soil types under diver management practices.

From a practical point of view, the active organic matter tests described herein are (1) instant, farmer-friendly, visually contrasting, and precise, (2) economic, non-toxic, reliable, and consistent, (3) correlate with soil quality indicators, (3) predict crop growth and yield, and (4) are a universal test for any soil types. The test kit described herein allows individuals to evaluate soil quality on site (e.g., right in their field) within a matter of minutes. The active organic matter test can be used to estimate total and active organic matter, calculate total and plant available (active) nitrogen for guiding nitrogen fertilization, measure soil biological health and enzyme activity, determine soil porosity and aggregate stability, predict crop growth and yield, evaluate overall soil quality/health, or any combination thereof.

The test can be used with a wide range of soils under variable management systems worldwide. The results of the colorimetric assay are clearly and rapidly visible, distinctly identifiable and measurable, and sensitive to management practices. The active organic matter test kit was calibrated and validated for its prediction accuracy using diverse soils from different long-term field experiments, representing a range of soils, tillage practices, crop diversity, and other management practices worldwide. The test results can be further transformed into a more sophisticated web-based tool, or a smartphone app, or as an add-on tool with other tools. The predictive capability of the active organic matter test to estimate and/or predict SOM content (soil carbon sequestration) provides a way to more accurately calculate credits, rewards, and compensation by the state, federal and private agencies involved in carbon trading.

Active Organic Matter (Carbon) Test

The active carbon test described herein can (1) be reliable to correlate with and predict soil quality indicators, (2) be a predictor of nitrogen fertilization (active nitrogen levels), (3) predict crop growth and yield, (4) be a sensitive, contrasting and precise test, and (5) be universally usable for any soils.

The new active carbon test uses a volume (e.g., 30 mL) of an aqueous solution containing 0.02M $KMnO_4$ (an oxidant), $CaCl_2$ and $Al(Cl)_3$ (inorganic flocculent), and $K_2HPO_4$ (a pH buffering agent) to adjust the pH of the solution to 6.0. The resulting test solves most of the shortcomings associated with existing colorimetric active carbon tests. In particular, the active carbon test can consistently account for any variations in soil quality under variable management practices in different soils worldwide.

Test Kit

An example test kit for assessing for assessing active organic matter can include the following:

A graduated plastic or glass tube (50 mL volume)
A graduated glass bottle or cuvette (20 mL volume)
A spoon for obtaining and measuring 5 g of air-dried soil
A plastic syringe or plastic tube (1 mL volume)
A Black plastic square (15 cm×15 cm)
A water bottle
A reagent composition
Optionally a sieve (e.g., a 2 mm plastic sieve)
Optionally a color chart, small digital colorimeter, or other means for interpreting the results of the colorimetric assay Reagent Composition The reagent composition can be a stock solution comprising $K_2HPO_4$ (Dipotassium Phosphate), $CaCl_2 \cdot 2H_2O$ (Calcium Chloride Dihydrate), $Al(Cl)_3$ (Aluminum Chloride) and $KMnO_4$ (Potassium Permanganate) buffered at pH 6.0. Alternatively, the reagent composition can be in a solid form (tablet or powder). The reagent composition can be prepared such that it can be dissolved and/or diluted to provide the desired concentration of components in the aqueous solution. Alternatively, the reagent composition can be a solution having the desired concentration of components in the aqueous solution.

In one example, the reagent composition can be a concentrated stock solution comprising 0.2M $KMnO_4$ (Potassium Permanganate), 1M $CaCl_2 \cdot 2H_2O$ (Calcium Chloride Dihydrate), 0.1M $Al(Cl)_3$ (Aluminum Chloride), and 0.01M $K_2HPO_4$ (Dipotassium Phosphate) buffered at pH 6.0. The $KMnO_4$ solution acts as a reactant (oxidizing agent) and an indicator, the $CaCl_2$ and $Al(Cl)_3$ act as flocculants to rapidly settle (precipitate) dispersed soil particles during the assay, and the $K_2HPO_4$ acts both as a pH buffer and a complexing agent which minimizes interference from the colored metal ions (e.g., iron) present in the soil.

The water used can be, for example, distilled, drinking, bottled, river, canal or rainwater.

The example stock solution can be prepared as described below. First, 147 g of $CaCl_2$ was massed into a 1000-mL volumetric flask, 500-mL of distilled water was added, and the $CaCl_2$ was dissolved (using magnetic stirrer, if needed). 13.34 g $Al(Cl)_3$ was added to the solution. The dissolution of $CaCl_2$ and $Al(Cl)_3$ generated heat (exothermic reaction), causing the solution temperature to rise. The increased temperature helped with the subsequent dissolution of $K_2HPO_4$ and $KMnO_4$. Next, 1.74 g $K_2HPO_4$ was added to $CaCl_2/Al(Cl)_3$ solution (using magnetic stirrer, if needed). Next, 31.61 g of $KMnO_4$ was added to the 1M $CaCL_2$ and 0.01M $K_2HPO_4$ solution and completely dissolved in the solution for preparing the colored reagent.

At this point, the solution pH was acidic (around pH 3). The solution pH was adjusted to 6.0 using dilute sodium hydroxide NaOH) solution (e.g., 1 or 0.05 M) Finally, the solution was diluted to around the 950-mL mark with distilled deionized water (pH 7). The final pH of the solution was checked and adjusted to a pH of 6.0 with 0.05M NaOH.

Test Procedure

Take a small representative soil sample at 0 to 7.5 cm from five different locations in the field (approx. 25 g or 5 tablespoonful). If sampling moist soil, crumble gently, mix, and spread thinly on the black card to air-dry for 10-15 minutes (preferably in direct sunlight). Crumble & mix the air-dried soil for even distribution or sieve with a small 2-mm plastic mesh (4-5 cm diameter) before proceeding.

Next, using the dropper, take 2-mL, of the reagent solution into the clean, graduated-glass mixing bottle.

Add distilled (or tap) water o the 20-mL mark & cap the bottle, then swirl the bottle to mix the solution thoroughly.

Add one level tablespoonful (or weigh 5 g) of uniformly mixed air-dried soil to the graduated-bottle with 20 or 30-mL reagent depends on the soil types.

Cap bottle tightly & shake vigorously (~100 strokes per min) for 2 minutes and then let the bottle stand for 5-10 minutes allowing soil to settle down.

Figure 1:
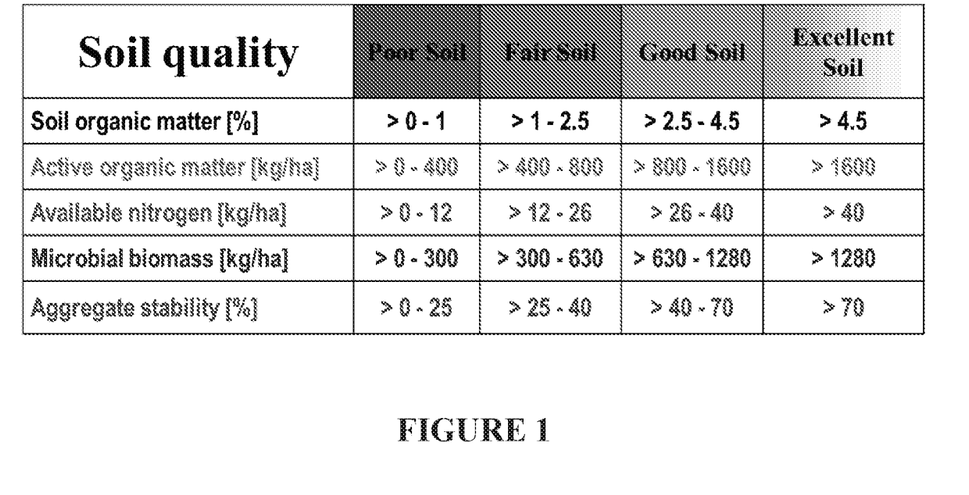
FIG. 1 is shows an example color chart correlating the color of the aqueous solution with soil quality (segmented as either poor, fair, good, or excellent), total soil organic matter (in weight percent), active organic matter (in kg/ha), active (available) nitrogen content (in kg/ha), microbial biomass (in kg/ha), and soil aggregate stability (in percent)

After 5-10 minutes, match the color of the solution (liquid in top of bottle) with the color chart provided (see, for example, FIG. 1) to estimate overall soil quality, active organic matter, and other parameters. If the solution appears colorless (no pink shade), the steps above are repeated except using 3 mL, of the reagent stock solution instead of 2 mL, and volume to 30-mL.

If a quantitative result is desired, the aqueous solution can be measured using a digital colorimeter (e.g., a HANNA Checker®).

Take a 50-mL plastic vial and fill the plastic vial with distilled (or tap) water to about 45 ml mark. Next, rinse the plastic dropper with water 2 to 3 times before use. Use the dropper to take 0.5 ml aliquot (liquid above settled soil) from the 20-ml graduated glass bottle with the dropper and add to the vial. Fill the vial with distilled (or tap) water up to 50 ml mark (shake to mix).

The HANNA Checker® has two glass vials—fill one vial (vial #1) with the distilled (or tap) water and the second glass vial (vial #2) with the light pink solution from the 50 ml plastic vial.

Clean both glass vials from outside with a microfiber cloth or paper towel.

Insert vial 41 in the HANNA Checker® and press the button. When the display shows "Add", "C.1" with "Press" blinking, the meter is ready.

Press the button again. When the display shows "Add", "C.2" with "Press" blinking the meter is zeroed, and ready to read the sample. Insert vial #2 in the HANNA Checker® and press the button. The instrument will show "- - - -" and display a reading corresponding to the sample.

Figure 2A:
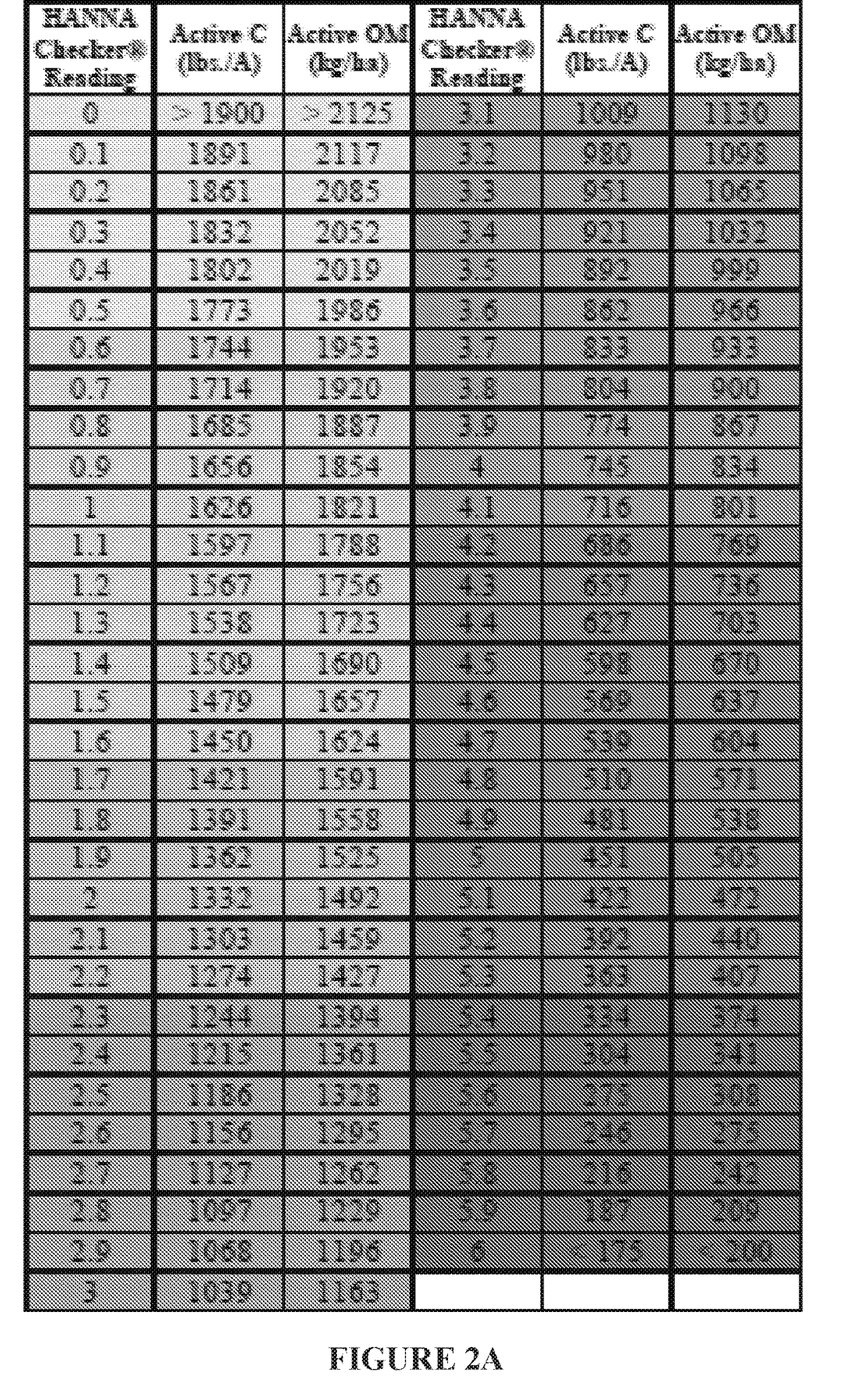
FIG. 2A shows a lookup table listing the concentration of active organic matter indicated with different colorimeter readings for solutions prepared using 2 mL of reagent stock solution.
Figure 2B:
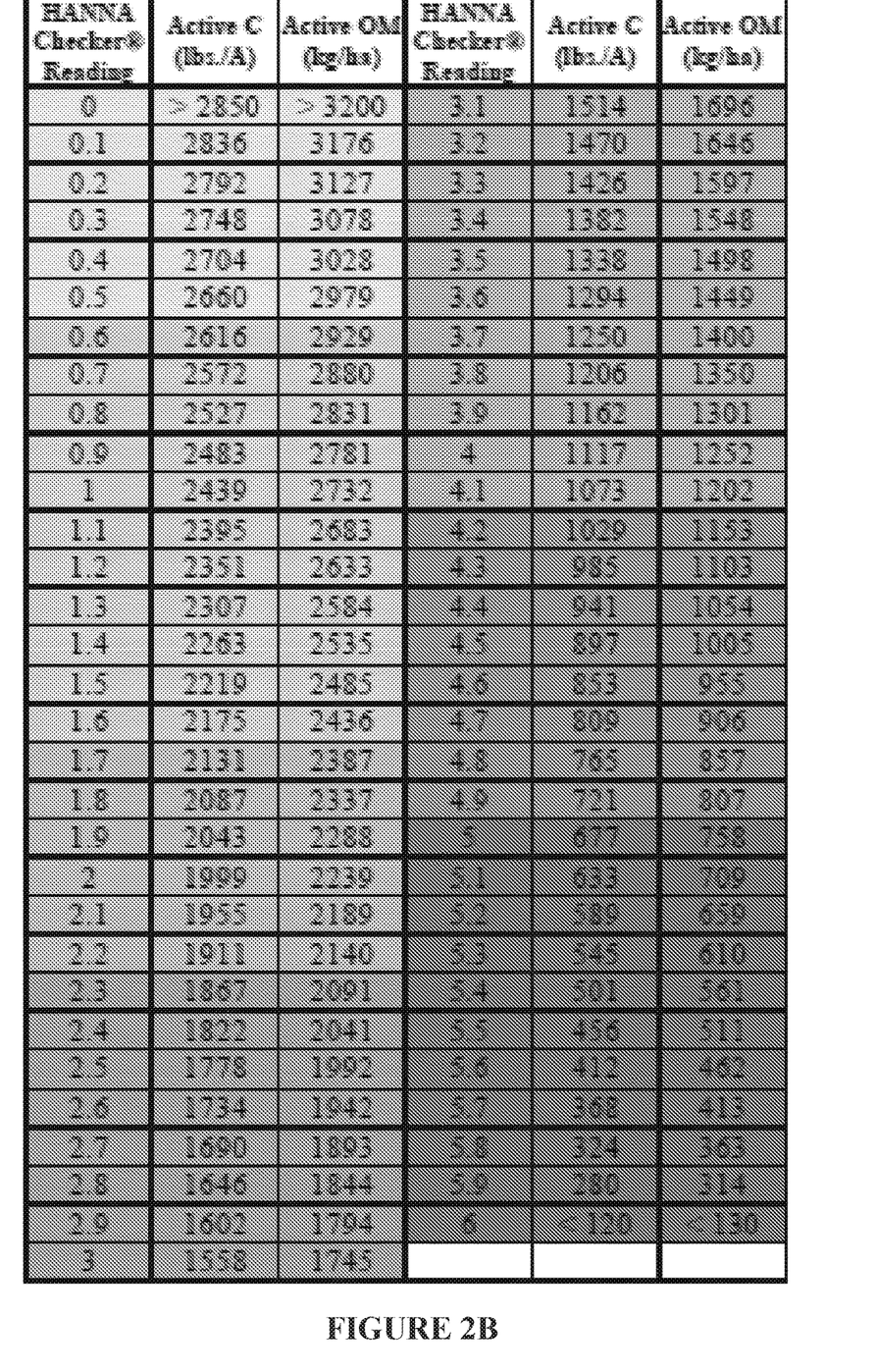
FIG. 2B shows a lookup table listing the concentration of active organic matter indicated with different colorimeter readings for solutions prepared using 3 mL of reagent stock solution.

The concentration of active carbon can then be calculated using a function derived from a standard curve or be using a lookup table correlating colorimeter readings to active organic matter (as shown in FIGS. 2A and 2B).

If desired, one or more additional soil quality parameters can be derived from the quantity of active carbon (active organic matter) in the soil sample. Microbial biomass, basal respiration, total nitrogen content, active nitrogen content, particulate organic carbon, aggregate stability, and soil quality (segmented excellent, good, fair, and poor) have all been correlated with active organic matter. Using these relationships, these additional soil quality parameters or their pedotransfer functions can be readily derived from the measured quantity of active carbon (active organic matter) in the soil sample. Further, projected crop yields and projected relative crop yields have also been correlated with active organic matter. Therefore, using these relationships, a projected crop yield and/or projected relative crop yield can be readily derived from the measured quantity of active carbon (active organic matter) in the soil sample.

Example 2

Stability of Active Carbon Test as a Measure of Soil Quality

In this example, our objective was to modify, calibrate and validate the stability of the active carbon test described above as a routine measure of soil quality. In particular, these efforts investigated (1) the effect of soil processing; (2) solution pH variations, buffering, and flocculants; (3) solution masking and clarity; (4) the effect of shaking time and amount of soil; and (5) the seasonal stability of the test.

Representative soils were collected from long-term research plots and farmers' fields under diverse management practices in Alabama, Arkansas, California, Florida, Illinois, Indiana, Kentucky, Maryland, Michigan, Mississippi, Missouri, North Carolina, Ohio, Pennsylvania, Virginia, and Wisconsin. The soils were analyzed for selected biological, chemical, and physical properties, including active C contents. Moreover, data on soil properties and active C collected from Bangladesh, Benin, Brazil, Burkina Faso, China, France, Ghana, India, Moldavia, Sierra Leone, Turkey, Ukraine, and Uzbekistan were included.

The following were evaluated experimentally:

Soil processing with grinding vs. 2-mm sieving effect.

$KMnO_4$ solution pH variations with single or mixture of flocculants.

Solution masking and clarity with- and without centrifugation (lab).

Shaking time and amount of soil (over- or underestimated).

Seasonal stability of active C test (reliability).

Figure 3:
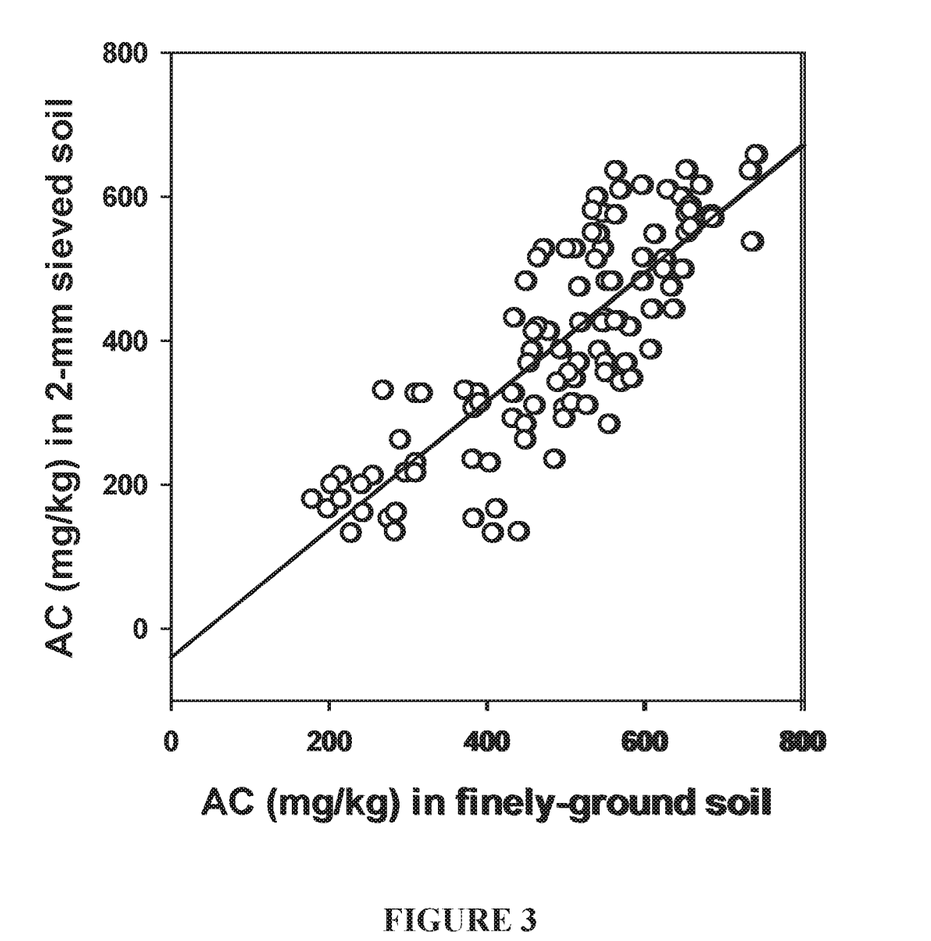
FIG. 3 is a plot showing the results of active C measurement in finely ground vs. 2-mm sieved, air-dried soils under contrasting management practices.

FIG. 3 is a plot showing the results of active C measurement in finely ground vs. 2-mm sieved, air-dried soils under contrasting management practices. Finely ground soils were found to significantly overestimate the active C content (by about 40 mg/kg soil), as compared with the 2-mm sieved soils. Accordingly, in some embodiments, the soil can be sieved prior to measurement.

Figure 4:
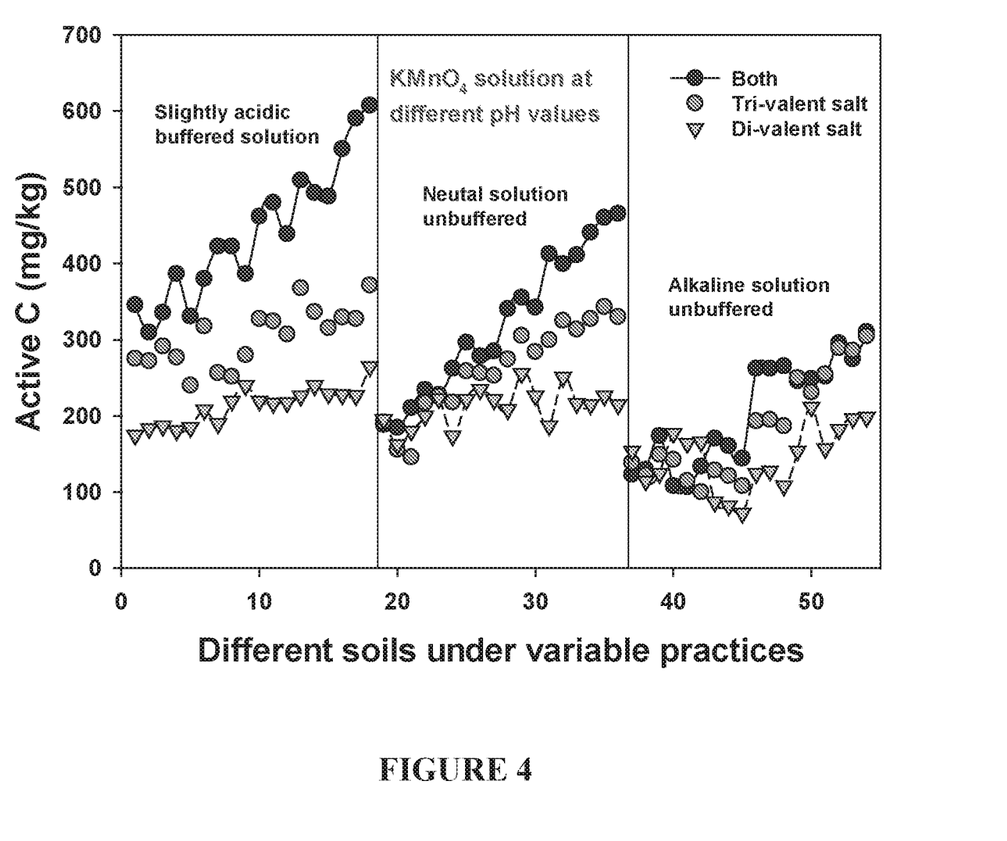
FIG. 4 is a plot showing the effects of $KMnO_4$ solution pH with- and without flocculants on active C measurement in soils under diverse management practices.

FIG. 4 is a plot showing the effects of $KMnO_4$ solution pH with- and without flocculants on active C measurement in soils under diverse management practices. Slightly acidic $KMnO_4$ solution (buffered) consistently detected significant variations in active C content of soils under contrasting management practices as compared to an existing active C test and its alkaline variant. The addition of trivalent salts or mixture of both di- and trivalent salts increased the clarity of solution more than that of the divalent salt, when used as a flocculant.

Figure 5:
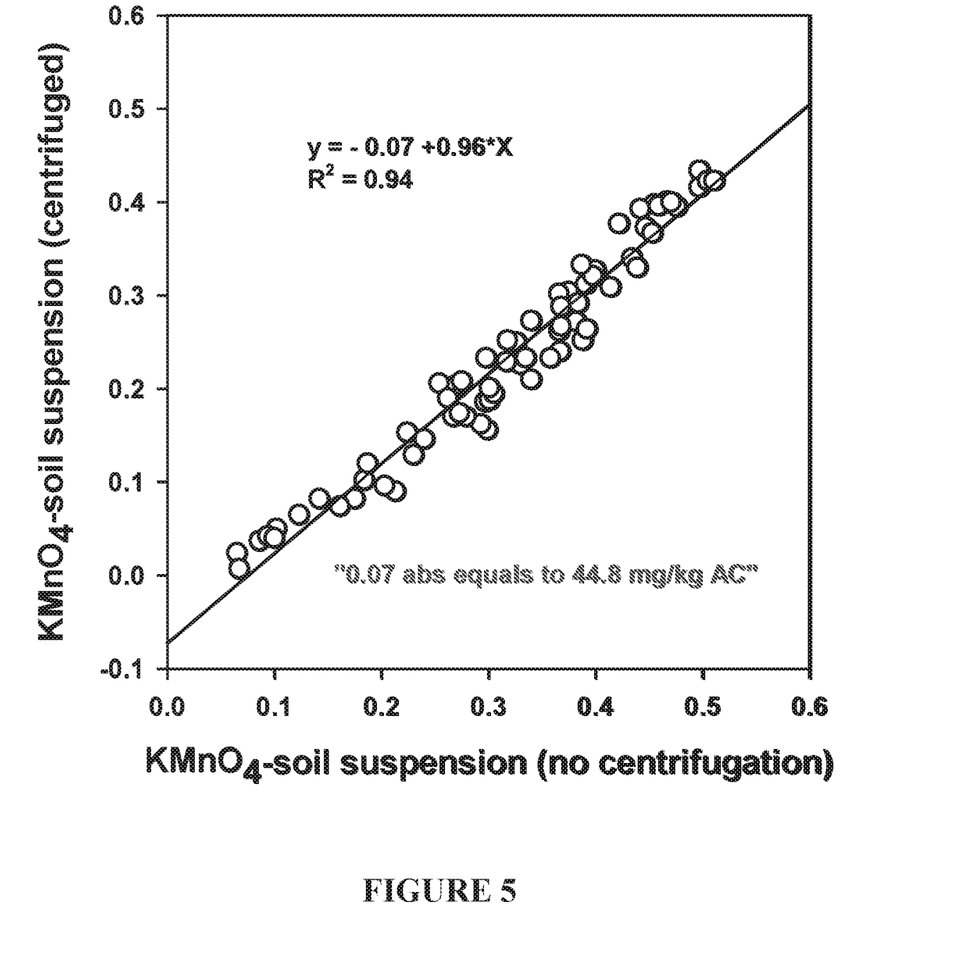
FIG. 5 is a plot showing the effects of centrifugation on solution absorbance of active C in soils under contrasting management practices.

FIG. 5 is a plot showing the effects of centrifugation on solution absorbance of active C in soils under contrasting management practices. The use of flocculent may not enough to clarify the solution when measuring active C in the lab. Without centrifugation, there may be an overestimation (by about 45 mg/kg) of active C results as a background noise. Accordingly, in some embodiments, centrifugation and/or filtration can be used to clarify the sample prior to analysis.

Figure 6:
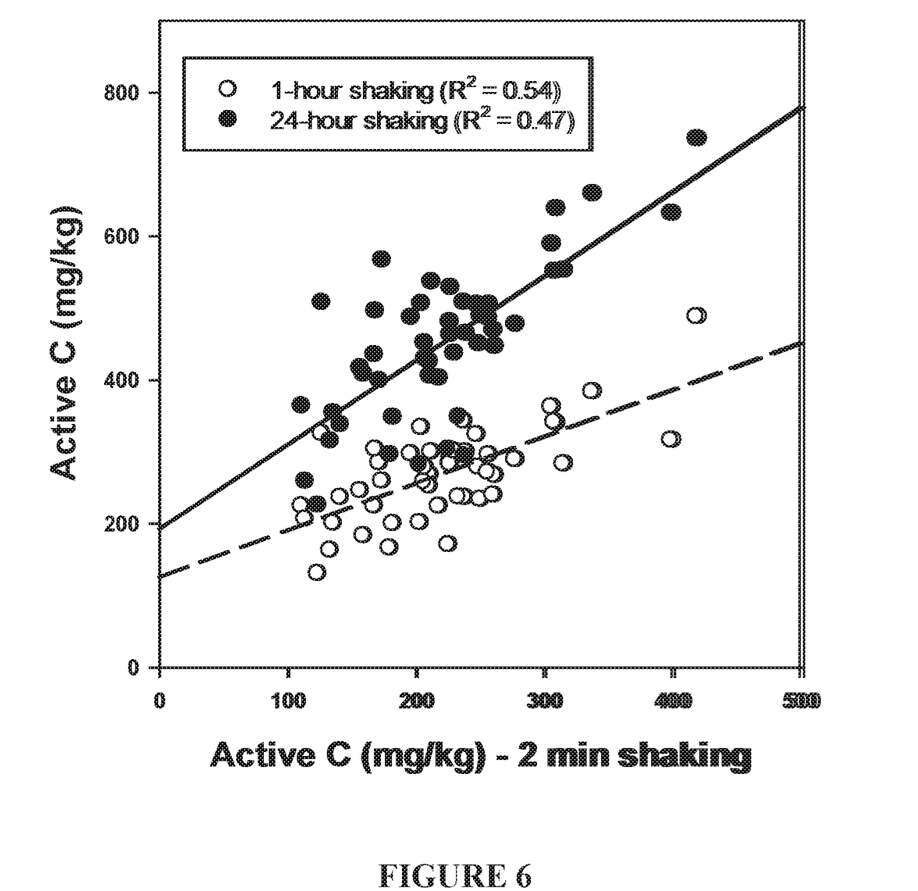
FIG. 6 is a plot showing the soil-$KMnO_4$ suspension shaking time effect on active C measurement in soils under contrasting management practices.
Figure 7:
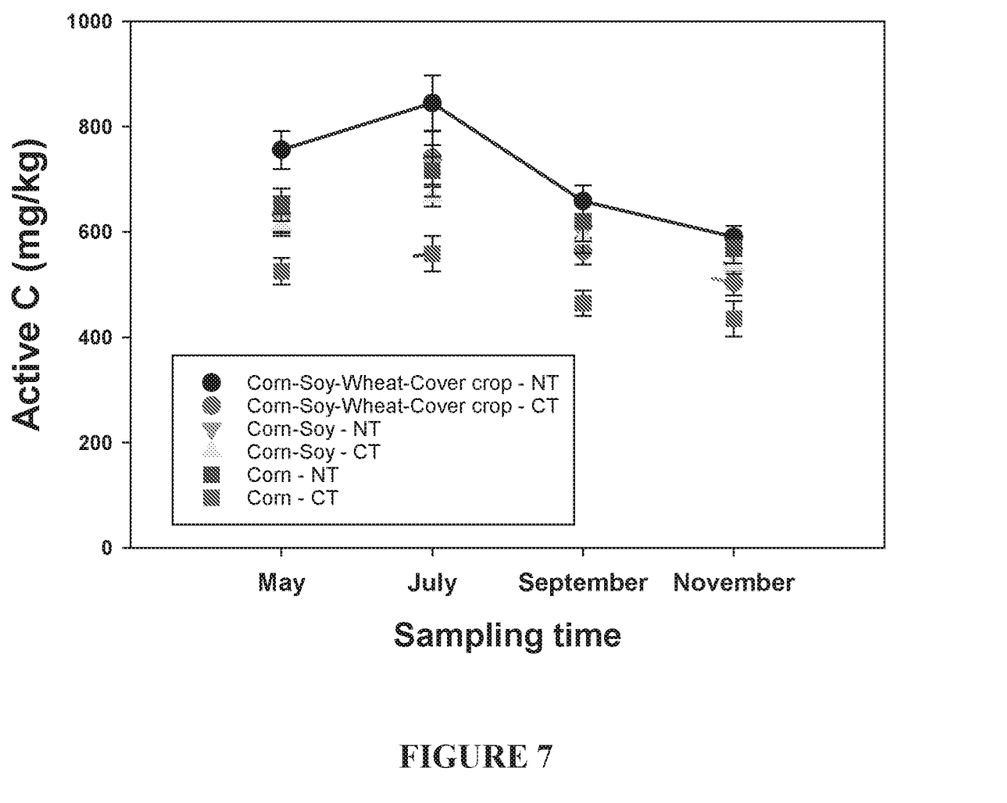
FIG. 7 is a plot showing the seasonal variations on active C measurement soils under contrasting tillage and cropping diversity systems.

FIG. 6 is a plot showing the soil-$KMnO_4$ suspension shaking time effect on active C measurement in soils under contrasting management practices. An hour or a 24-hour shaking of soil-$KMnO_4$ solution will overestimate the active C contents. Accordingly, in some embodiments, the sample can be shaken or agitated for less than one hour (e.g., less than thirty minutes, or less than fifteen minutes), FIG. 7 is a plot showing the seasonal variations on active C measurement in soils under contrasting tillage and cropping diversity systems. Seasonal variations slightly affected the active C test results; however, the pattern of the active C results was similar under diverse management practices.

The kits and methods of the appended claims are not limited in scope by the specific kits and methods described herein, which are intended as illustrations of a few aspects of the claims. Any kits and methods that are functionally equivalent are intended to fall within the scope of the claims. Various modifications of the kits and methods in addition to those shown and described herein are intended to fall within the scope of the appended claims. Further, while only certain representative kits and method steps disclosed herein are specifically described, other combinations of the kits and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising", and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference,

What is claimed is:

1. A method for assessing a quantity of active organic matter in a soil sample, the method comprising:
   (a) contacting a soil sample with an aqueous solution comprising a permanganate salt, an inorganic flocculant, and a pH buffering agent, wherein the aqueous solution is buffered at a pH of from 5 to less than 7; and
   (b) evaluating the aqueous solution to assess the quantity of active organic matter in the soil sample.

2. The method of claim 1, wherein the permanganate salt comprises potassium permanganate.

3. The method of claim 1, wherein the permanganate salt is present in the aqueous solution at a concentration of from 0.01 M to 0.05 M.

4. The method of claim 1, wherein the aqueous solution has is buffered at a pH of from 5.5 to 6.5.

5. The method of claim 1, wherein the pH buffering agent also acts as an inorganic complexing agent.

6. The method of claim 1, wherein the pH buffering agent is present in the aqueous solution at a concentration of from 0.0005 M to 0.01 M.

7. The method of claim 1, wherein the inorganic flocculant is present in the aqueous solution at a concentration of from 0.01 M to 0.2 M.

8. The method of claim 1, wherein the inorganic flocculant exhibits a positive enthalpy of solvation in water.

9. The method of claim 1, wherein step (b) comprises:
   visually comparing a color of the aqueous solution with a color chart to determine the concentration of active organic matter in the soil sample, wherein the color chart comprising a plurality of colors and a concentration of active organic matter corresponding to each of the plurality of colors;
   measuring an absorbance value of the aqueous solution using a spectrophotometer, and determining the concentration of active organic matter in the soil sample from the absorbance value using a standard curve that correlates absorbance values at a wavelength with concentrations of active organic matter in soil samples;
   measuring an absorbance value of the aqueous solution using a colorimeter, and determining the concentration of active organic matter in the soil sample from the absorbance value using a lookup table that lists concentrations of active organic matter in soil samples for a plurality of absorbance values;
   imaging the aqueous solution, obtaining one or more RGB values from an image of the aqueous solution, and determining the concentration of active organic matter in the soil sample from the one or more RGB values using a lookup table that lists concentrations of active organic matter in soil samples for a plurality of RGB values; or
   imaging the aqueous solution, obtaining one or more RGB values from an image of the aqueous solution, and determining the concentration of active organic matter in the soil sample from the absorbance value using a standard curve that correlates one or more RGB values with concentrations of active organic matter in soil samples.

10. The method of claim 1, further comprising deriving one or more additional soil quality parameters from the quantity of active organic matter in the soil sample,
   wherein the one or more additional soil quality parameters are selected from the group consisting of microbial biomass, basal respiration, total nitrogen content, active nitrogen content, particulate organic carbon, aggregate stability, soil quality, or any combination thereof.

11. The method of claim 1, further comprising deriving a projected crop yield or projected relative crop yield from the quantity of active organic matter in the soil sample.

12. The method of claim 1, wherein the soil sample comprises an oxisol, a mollisol, an alfisol, an ultisol, an entisol, an inceptisol, or any combination thereof.

13. The method of claim 1, wherein the pH buffering agent comprises a phosphate salt.

14. The method of claim 13, wherein the phosphate salt comprises dipotassium phosphate.

15. The method of claim 1, wherein the inorganic flocculant comprises a chloride salt.

16. The method of claim 15, wherein the chloride salt is selected from the group consisting of calcium chloride, aluminum chloride, and combinations thereof.

17. The method of claim 1, wherein step (a) comprises:
   (i) combining the soil sample and the aqueous solution in a vessel;
   (ii) agitating the soil sample and the aqueous solution; and
   (iii) incubating the soil sample and the aqueous solution.

18. The method of claim 17, wherein step (iii) comprises incubating the soil sample and the aqueous solution for a period of time sufficient to allow the soil sample to settle out of the aqueous solution and a color of the aqueous solution to equilibrate.

19. A method for cultivating a crop in an agricultural field, the method comprising:
   planting the crop in the agricultural field;
   allowing the crop to reach at least a seedling stage;
   collecting a soil sample from the agricultural field;
   determining a quantity of active organic matter in the soil sample using the method of claim 1;
   deriving a quantity of active nitrogen in the soil sample from the quantity of active organic matter measured in the soil sample; and
   applying a fertilizer to the agricultural field when the quantity of active nitrogen in the soil sample is less than 1600 kg/ha.

* * * * *